US009598817B2

United States Patent
Wedell et al.

(10) Patent No.: US 9,598,817 B2
(45) Date of Patent: Mar. 21, 2017

(54) DARK SHADE DYEING METHOD FOR MICROPOROUS TRACK ETCH MEMBRANES WITH LARGE PORES AND LOW POROSITY

(71) Applicant: CORNING INCORPORATED, Corning, NY (US)

(72) Inventors: Gabriele Wedell, Bannewitz (DE); Michael Stiebitz, WeiBnauBlitz (DE)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 14/388,296

(22) PCT Filed: Apr. 1, 2013

(86) PCT No.: PCT/US2013/034817
§ 371 (c)(1),
(2) Date: Sep. 26, 2014

(87) PCT Pub. No.: WO2013/151936
PCT Pub. Date: Oct. 10, 2013

(65) Prior Publication Data
US 2015/0072410 A1    Mar. 12, 2015

Related U.S. Application Data

(60) Provisional application No. 61/619,033, filed on Apr. 2, 2012.

(51) Int. Cl.
| | |
|---|---|
| *C12M 1/12* | (2006.01) |
| *D06P 3/54* | (2006.01) |
| *D06P 1/18* | (2006.01) |
| *D06P 1/20* | (2006.01) |
| *C08J 7/06* | (2006.01) |
| *D06P 5/20* | (2006.01) |

(52) U.S. Cl.
CPC .............. *D06P 3/54* (2013.01); *C08J 7/065* (2013.01); *D06P 1/18* (2013.01); *D06P 1/20* (2013.01); *D06P 5/2077* (2013.01); *C08J 2367/02* (2013.01); *C12M 25/02* (2013.01)

(58) Field of Classification Search
CPC ...... D06P 1/18; D06P 1/20; D06P 3/54; D06P 5/2077; C08J 7/065; C08J 2367/02; C12M 25/02
USPC ....................................................... 435/297.1
See application file for complete search history.

(56) References Cited

U.S. PATENT DOCUMENTS

| | | | |
|---|---|---|---|
| 3,337,289 A | 8/1967 | Manwaring | |
| 5,338,318 A * | 8/1994 | Mercado | ............. D06P 1/65125 8/495 |
| 5,362,812 A | 11/1994 | Holmes et al. | |
| 2003/0182737 A1* | 10/2003 | Inoue | ....................... D06P 1/16 8/506 |
| 2006/0134397 A1 | 6/2006 | Smith | |
| 2010/0233329 A1 | 9/2010 | Marno | |

FOREIGN PATENT DOCUMENTS

| | | |
|---|---|---|
| CN | 1034329 | 8/1989 |
| CN | 1804205 | 7/2006 |
| CN | 101386473 | 5/2011 |
| GB | 1 034 558 | 6/1966 |

OTHER PUBLICATIONS

International Search Report of PCT/US2013/034817 dated Jun. 21, 2013.

* cited by examiner

*Primary Examiner* — Eisa Elhilo
(74) *Attorney, Agent, or Firm* — Susan S. Wilks; Hoffman and Barron, LLP

(57) ABSTRACT

Methods for dyeing of microporous track etched membranes are provided. In particular, these methods are suitable for dark shade dyeing of membranes having large pores with low porosity. Desirably, such methods provide dyed membranes wherein the membrane parameters are not significantly changed as compared to those prior to dyeing. Likewise, the resultant dyed membranes exhibit no negative influence on sensitive cell culture system applications.

14 Claims, No Drawings

DARK SHADE DYEING METHOD FOR MICROPOROUS TRACK ETCH MEMBRANES WITH LARGE PORES AND LOW POROSITY

CROSS-REFERENCE TO RELATED APPLICATIONS

This application is a U.S. National Stage filing under 35 U.S.C. §371 of International Application No. PCT/US2013/034817, filed Apr. 1, 2013, which in turn claims priority to U.S. Provisional Patent Application No. 61/619,033 filed on Apr. 2, 2012, the entire contents of which are incorporated by reference herein.

FIELD OF THE INVENTION

The present invention relates to methods for dyeing microporous track etched membranes. In particular, methods for dark shade dyeing membranes having a pore diameter greater to or equal to 0.8 µm.

BACKGROUND OF THE INVENTION

Generally, dyeing processes for microporous polyester track etched membranes having pores with a diameter of less than 0.8 µm (so-called "small pore") and high porosity employ disperse dyes in aqueous/alcoholic systems, followed by fixation of the dye and removal of residual dye from the membrane surfaces by reducing with sulfite-containing solutions or washing with appropriate solvents or surfactants. Due to the large number of pores with individually dyed walls, it is possible to achieve dark shades of color using this technique.

In contrast, membranes having pores wherein the largest pore size has a diameter greater to or equal to 0.8 µm (so-called "large pore") and low porosity have relatively fewer inner pores and wall surfaces. As such, to achieve a dark shade which substantially blocks transmission at one or more wavelengths, it is essential to dye the membrane material itself much more so as compared to membranes having small pores and high porosity. Although the use of disperse dyes in solvent systems having higher boiling alcohols or other hydrocarbons may be employed to achieve this result, removal of such solvents is difficult and can negatively influence cell culture which is a common application of such membranes. Additionally, relatively high temperatures that typically exceed the glass transition temperature of the membrane material, such as polyethylene terephthalate (PET), are employed to move the dye molecules through the polymer chains to get a substantial dyeing effect. However, this approach often results in structural changes of the membrane material which can result in a change of membrane parameters such as pore diameter or surface roughness. Thus, there is a need for improved methods to achieve dark shade dyeing for microporous track etch membranes with large pores and low porosity.

SUMMARY OF THE INVENTION

The present invention provides methods for dyeing microporous membranes. Such methods are particularly suitable for dark shade dyeing of membranes having large pores with low porosity. Desirably, these methods employ aqueous systems wherein the resultant membrane parameters are not significantly changed as compared to those prior to dyeing. Likewise, the resultant dyed membranes exhibit no negative influence on sensitive cell culture system applications.

In one aspect, the present invention provides methods for dyeing a microporous membrane including: contacting the membrane with an aqueous dispersion dye system at a temperature between 90 to 100° C. for a time period sufficient to produce a desired transmission spectra for the membrane wherein the aqueous dispersion dye system includes a dyeing additive and a dye selected from the group of azo and anthraquinone dyes, and heating the membrane by exposing it to a temperature between 110 and 150° C. for 20 to 90 minutes thereafter.

In another aspect, the present invention provides dyed membranes prepared in accordance with any of the methods of the present invention.

In yet another aspect, the present invention provides cell culture systems including membranes dyed in accordance with any of the methods of the present invention.

These and other features of the invention will be better understood through a study of the following detailed description.

DETAILED DESCRIPTION OF THE INVENTION

As used herein the following terms shall have the definitions set forth below.

As used herein, the phrase "large pore(s)" refers to a membrane wherein the largest pore size present therein has a diameter greater than or equal to 0.8 µm.

As used herein, the phrase "low porosity" refers to a membrane having a relatively low number of pores per unit area of the membrane. In contrast, the phrase "high porosity" refers to a membrane having a relatively high number of pores per unit area of the membrane.

As used herein, the phrase "substantially blocks transmission" with regard to a membrane refers to at least a 90% reduction in the transmission of light at one or more wavelengths, more preferably at least a 95% reduction in the transmission of light at one or more wavelengths.

Provided are methods for dyeing a microporous membrane comprising: contacting the membrane with an aqueous dispersion dye system at a temperature of about 100° C. for a time period sufficient to produce a desired transmission spectra for the membrane wherein the aqueous dispersion dye system comprises a dyeing additive and a dye selected from the group of azo and anthraquinone dyes, and heating the membrane by exposing it to a temperature between 110 and 150° C. for 20 to 90 minutes thereafter to fix the dye absorbed in the membrane. Preferably, the membrane, following heating, is contacted with a solvent to remove residual dye from surfaces of the membrane.

In one embodiment, the membrane is contacted with the aqueous dispersion dye system at a temperature of about 100° C. for a time period between 20 and 90 minutes.

In one embodiment, heating the membrane to fix the dye therein employs a heated film transportation cylinder. Notably, fixation results in the diffusion of dye into the polymer matrix.

Residual dye at the surfaces of the membrane are removed by reducing with a sulfite-containing agent (e.g., REDULIT RED or MEROPAN RED both available from CHT Bezema (Germany), ERIOPON RC available from Huntsman (Singapore) or PERIGEN THD available from Dr. Petry (Germany)) or a non-sulfite containing solvent which is alkaline, (e.g., PERISTAL RCV available from Dr. Petry (Germany)

or REDULIT GIN available from CHT Bezema (Germany)); and subsequent washing with water having a temperature between 40 to 70° C.

In one embodiment, the solvent includes a sulfite-containing agent. In another embodiment, the solvent is alkaline. In one embodiment, the solvent has an alkalinity between pH 11 to 13. In yet another embodiment, the solvent is selected from a ketone, an aldehyde, an ether, an ester, an alcohol or a combination of two or more thereof. Exemplary suitable solvents include, but are not limited to, ethanol, butanol, ethylacetate, butylacetate, acetone, or a combination of two or more thereof.

In one embodiment, the solvent is an aqueous system.

Treatment with the solvent occurs at a temperature between 10 to 25° C. so as to prevent diffusion of the solvent into the polymer.

In still yet another embodiment, the methods further include washing surfaces of the membrane with water, preferably having a temperature between 40 to 70° C., subsequent to contacting the membrane with the solvent. Furthermore, in one embodiment, the methods further include drying the membrane following washing the surfaces thereof. In one embodiment, air at a temperature between 100 to 160° C. is used to dry the membrane.

In one embodiment, the method further includes online measurement of the membrane's transmission spectra.

Advantageously, the methods for dyeing microporous membrane described herein are suitable for a continuous roll-to-roll process with final online control of the transmission spectra of the dyed membrane.

Dyes suitable for use in the methods of the present invention are disperse dyes selected from azo and anthraquinone chemical classes. In particular, dyes having relatively small molecules with a molar mass between 700 to 900 g/mol are preferred. Exemplary dyes for use in the methods of the present invention include, but are not limited to, the Terasil dye family (e.g., TERASIL BLACK BFE, TERASIL BLUE BGE; available from Huntsman, Singapore) the Bemachron dyes (available from CHT Bezema, Germany) and the Fantagen dyes (available from Farbchemie Braun, Germany). Preferably, the amount of dye(s) for use in the methods of the present invention is between 4 and 15% wt/vol. In certain embodiments, one or more dyes include those from the Terasil dye family (available from Huntsman, Singapore) in an amount between 4 and 15% wt/vol.

It is understood by those skilled in the art that to achieve a desired transmission spectra, dyes can be mixed, or blended. Alternatively, to achieve the transmission spectra desired, the membrane can be subjected to more than one aqueous dye dispersion system having different dye(s) therein. For example, to achieve a total cover of the spectral region between 350 and 700 nm in a membrane, a combination of dyes may be employed such as black, blue and red or orange dyes. In one embodiment, the dye is black, blue, red, orange or a combination of two or more thereof. In another embodiment, the dyes employed are blue and red. In yet another embodiment, the dyes employed are blue and orange.

The aqueous dispersion dye system includes at least one dyeing additive. Exemplary dyeing additives include, but are not limited to, carriers, equalizers, diffusion accelerators (e.g., UNIVADINE DFM or UNIVADINE DIF both available from Huntsman (Singapore)), dispersing agents, surfactants, defoamers and dedusting agents. Desirably, at least one dyeing additive added to the aqueous dispersion dye system assists in obtaining uniform adsorption of the dye to the membrane surface and/or enhances the diffusion of the dye molecules between the polymer chains of the membrane. Preferably, the amount of dyeing additive for use in the methods of the present invention is between 0.5 and 3% wt/vol.

In one embodiment, the dyeing additive is selected from the group consisting of a carrier, an equalizer, a diffusion accelerator or a combination of two or more thereof. Exemplary dyeing additives include, but are not limited to, UNIVADINE DFM or UNIVADINE DIF both available from Huntsman (Singapore), COLORCONTIN available from CHT Bezema (Germany), PERIGEN CU or PERIGEN CD both available from Dr. Petry (Germany). In one embodiment, the dyeing additive is a carrier. In certain embodiments, the carrier is glycerol triacetate. In yet another embodiment, the dyeing additive is a diffusion accelerator. In certain embodiments, one or more dyeing additives include diffusion accelerator(s) available from Huntsman (Singapore) in an amount between 0.5 and 3% wt/vol.

Additionally, in certain embodiments, one or more dyes include those from the Terasil dye family (available from Huntsman, Singapore) in an amount between 4 and 15% wt/vol and one or more dyeing additives include diffusion accelerator(s) available from Huntsman (Singapore) in an amount between 0.5 and 3% wt/vol.

Membranes suitable for use in the present invention include thermoplastic polymer(s) in their composition and are non-fibrous. Exemplary thermoplastic polymers include, but are not limited to, polyethylene terephtalate, poly(vinyl chloride), poly(vinyl) alcohol and polystyrene. In one embodiment, the membrane includes polyethylene terephtalate (PET).

Membranes suitable for use in the present invention have a plurality of pores therein disposed substantially perpendicular to the plane of the membrane. Pores of suitable size can be produced by any known process, for example by track etching. In one preferred embodiment, membranes have a pore diameter greater to or equal to 0.8 µm ("large pore").

Such methods are particularly suitable for dark shade dyeing of microporous track etched membranes having large pores with low porosity. For example, for preparing dyed membranes with a pore diameter greater or equal to 0.8 µm.

Preferably, the transmission spectra of a membrane dyed in accordance with any of the aforementioned methods is reduced by at least 75% relative to the membrane prior to dyeing, more preferably by at least 90%. Such dyed membranes are desirable for use as a fluorescence blocking filter.

Also provided are dyed membranes prepared in accordance with the methods described herein. In one embodiment, such dyed membranes substantially block transmission of one or more wavelengths. In another embodiment, such dyed membranes have a pore diameter greater or equal to 0.8 µm.

Advantageously, dyed membranes prepared in accordance with the methods described herein are suitable for use in cell culture system applications.

In one aspect (1), the disclosure provides methods for dyeing a microporous membrane including: contacting the membrane with an aqueous dispersion dye system at a temperature between 90 to 100° C. for a time period sufficient to produce a desired transmission spectra for the membrane wherein the aqueous dispersion dye system includes a dyeing additive and a dye selected from the group of azo and anthraquinone dyes, and heating the membrane by exposing it to a temperature between 110 and 150° C. for 20 to 90 minutes thereafter.

In an aspect (2), the disclosure provides the invention of aspect (1), wherein the time period is 20 to 90 minutes.

In an aspect (3), the disclosure provides the invention of aspect (1), wherein the dye is present at a concentration between 4 and 15% wt/vol.

In an aspect (4), the disclosure provides the invention of aspect (1), wherein the dyeing additive is present at a concentration between 0.5 and 3% wt/vol.

In an aspect (5), the disclosure provides the invention of any one aspects (1)-(4), wherein the dyeing additive is selected from the group consisting of a carrier, an equalizer, a diffusion accelerator or a combination of two or more thereof.

In an aspect (6), the disclosure provides the invention of any one aspects (1)-(5), wherein the dyeing additive is a carrier.

In an aspect (7), the disclosure provides the invention of any one aspects (1)-(5), wherein the dyeing additive is a diffusion accelerator.

In an aspect (8), the disclosure provides the invention of any one aspects (1)-(7), wherein the heating employs a heated film transportation cylinder.

In an aspect (9), the disclosure provides the invention of any one aspects (1)-(8), further comprising contacting the membrane, following heating, with a solvent to remove residual dye from surfaces of the membrane.

In an aspect (10), the disclosure provides the invention of aspect (9), wherein the solvent includes a sulfite-containing agent.

In an aspect (11), the disclosure provides the invention of aspect (9), wherein the solvent is alkaline.

In an aspect (12), the disclosure provides the invention of aspect (9), wherein the solvent is selected from a ketone, an aldehyde, an ether, an ester, an alcohol or a combination of two or more thereof.

In an aspect (13), the disclosure provides the invention of aspect (9), further comprising washing surfaces of the membrane with water subsequent to contacting the membrane with the solvent.

In an aspect (14), the disclosure provides the invention of aspect (13), further comprising drying the membrane following washing the surfaces thereof.

In an aspect (15), the disclosure provides the invention of aspect (1), further comprising online measurement of the membrane's transmission spectra.

In an aspect (16), the disclosure provides the invention of aspect (1), wherein the dye is black, blue, red, orange or a combination of two or more thereof.

In an aspect (17), the disclosure provides a dyed membrane prepared in accordance with the method described in the invention of aspect (1).

In an aspect (18), the disclosure provides the invention of aspect (17), wherein the dyed membrane substantially blocks transmission of one or more wavelengths.

In an aspect (19), the disclosure provides the invention of aspect (17), wherein the dyed membrane has a pore having a diameter greater or equal to 0.8 μm.

In an aspect (20), the disclosure provides a cell culture system comprising a membrane dyed in accordance with the method described in the invention of aspect (1).

In an aspect (21), the disclosure provides the invention of any one aspects (1)-(4), wherein the dyeing additive is a carrier.

In an aspect (22), the disclosure provides the invention of any one aspects (1)-(4), wherein the dyeing additive is a diffusion accelerator.

In an aspect (23), the disclosure provides the invention of aspect (1), further comprising contacting the membrane, following heating, with a solvent to remove residual dye from surfaces of the membrane.

EXAMPLES

An aqueous dyeing solution was prepared by mixing 4 to 15% wt/vol TERASIL BLACK BFE, 0.5 to 5% wt/vol TERASIL BLUE BGE, 0.5 to 5% wt/vol Univadine DIF and 5 to 10% wt/vol acetic buffer pH 4.5. The aqueous dyeing solution was heated to a temperature between 90 to 100° C. Membrane was added to the aqueous dyeing solution at a temperature of about 100° C. and incubated for 20 to 60 min with continuous stirring thereof. Subsequently, the membrane was baked at a temperature between 110 and 150° C. for 20 to 90 minutes to absorb and fix the dye therein. At this juncture, two alternative treatments to remove residual dye from the surfaces of the membrane may be employed.

In one approach, the membrane is contacted with 1 to 5% wt/vol Redulit GIN in alkaline aqueous solution (pH 11 to 13) at a temperature between 60 to 80° C. for 15 to 30 min to reduce residual dye present therein. Subsequently, the membrane is washed with water at a temperature between 40 to 60° C. until clear, then dried with air at a temperature between room temperature (about 22° C.) and 60° C. In one embodiment, the membrane is dried with air at a temperature between 40 to 60° C.

Alternatively, the membrane is contacted with an organic solvent, e.g., ethyl acetate or acetone at a temperature between 10 to 25° C. for about 15 min, followed by washing with water at a temperature between 90 to 100° C. until clear. Subsequently, the membrane is dried with air at a temperature between room temperature (about 22° C.) and 60° C. In one embodiment, the membrane is dried with air at a temperature between 40 to 60° C.

Comparison of Membrane Parameters and Performance Following Dyeing Process

PET track etched membranes were dyed and membrane parameters as well as performance thereof compared to such membranes prior to dyeing. In particular, two different sized membranes were examined. One membrane having pores with a diameter of 8 μm, pore density of about 5E+04 pores/cm$^2$ and thickness of about 17 μm. The other membrane having pores with a diameter of 3 μm, pore density of about 6E+05 pores/cm$^2$ and thickness of about 20 μm. Both such membranes having the same base film material. In brief, PET track etched membranes were dyed using a dyeing solution with 25 to 40 g/L Terasil Black BFE, 6 to 10 g/L Terasil Blue BGE-01, 6 to 15 g/L Univadine DIF and 50 to 100 ml/L of a pH 4.5 acetate buffer. Small sheets of membranes were plunged into dyeing solution at 90 to 100° C. for 30 min to 1 hour during which time the solution was stirred continuously. The dyed membranes were subsequently air dried at room temperature. Dyed membranes were baked at 130 to 150° C. for 30 min to 1 hour. The redundant dye was removed from the surfaces of the dyed membranes by washing with a solvent, such as ethylacetate, acetone or an alcohol, at room temperature until the surfaces appeared clean, followed by washing with boiling water. The dyed membranes were subsequently air dried at room temperature.

To measure membrane thickness, flat pieces of the membranes were positioned on a small even ceramic plate and the thickness of the membranes measured with an inductive indicating calliper (Extramess by Mahr, Germany) by tipping the measuring point of the caliper on the flat membrane.

Thickness was measured at 5 points of the membranes. Medium thickness was calculated and documented with measured tolerances. For both membranes, thickness was in the same range before and after dyeing.

Additionally, track etched polyethylene terephthalate membrane dyed in accordance with the method described above exhibited no change in pore size and shape thereof as compared to that exhibited prior to dyeing. In particular, a clear membrane having pores with a diameter of 7.7±0.4 µm prior to dyeing exhibited pore diameter in the same range (i.e., 7.7±0.4 µm) subsequent to dyeing. Likewise, a membrane having pores with a diameter of 3.2±0.2 µm prior to dyeing exhibited the same pore size after dyeing.

For the measurement of air flow, lab equipment with membrane holder, manometer, mass flow meter and valves was used. Specifically, the measurement instruments used were mass flow meters with range of 0-500 ml/min and 0-2000 ml/min, both of Omega FMAxx series, and a manometer with 0-70 mbar, MH28 by Thommen Membrane discs were placed in the holder, having a free membrane area with 6 mm diameter. After closing the holder the inlet valve was opened. An appropriate air flow was adjusted to get measurement values in the upper quarter of the measurement ranges of the instruments. Air flow and pressure were documented and standardized air flow data in unit L/min cm$^2$ bar were calculated and documented. For each measured membrane three values were obtained. Medium air flows were calculated and documented with tolerances. For both membranes, air flow was in the same range before and after dyeing.

Furthermore, no negative affect was observed on sensitive cell culture system applications using membranes dyed in accordance with the method described above. In particular, a 56-hour assay was conducted using human umbilical cord vein endothelial cells and a membrane having pores with a diameter of 8 µm dyed as described above. Desirably, the dyed membrane exhibited very good performance and no negative influence of the dyeing process was observed.

It will be appreciated by those skilled in the art that changes could be made to the embodiments described above without departing from the broad inventive concept thereof. It is understood, therefore, that this invention is not limited to the particular embodiments disclosed, but is intended to cover modifications that are within the spirit and scope of the invention, as defined by the appended claims.

What is claimed is:

1. A method for dyeing a microporous membrane comprising:
   contacting the microporous membrane with an aqueous dispersion dye system at a temperature between 90 to 100° C. for a time period sufficient to produce a desired transmission spectra for the microporous membrane wherein the aqueous dispersion dye system comprises a dyeing additive comprising a diffusion accelerator; and a dye selected from the group of azo and anthraquinone dyes, and
   heating the dyed microporous membrane by exposing it to a temperature between 110 and 150° C. for 20 to 90 minutes thereafter.

2. The method of claim 1, wherein the heating step employs a heated film transportation cylinder.

3. The method of claim 1, further comprising contacting the membrane, following heating, with a solvent to remove residual dye from surfaces of the membrane.

4. The method of claim 3, wherein the solvent includes a sulfite-containing agent.

5. The method of claim 3, wherein the solvent is alkaline.

6. The method of claim 3, wherein the solvent is selected from a ketone, an aldehyde, an ether, an ester, an alcohol or a combination of two or more thereof.

7. The method of claim 3, further comprising washing surfaces of the membrane with water subsequent to contacting the membrane with the solvent.

8. The method of claim 7, further comprising drying the membrane following washing the surfaces thereof.

9. The method of claim 1, further comprising online measurement of the membrane's transmission spectra.

10. The method of claim 1, wherein the dye is black, blue, red, orange or a combination of two or more thereof.

11. A dyed membrane prepared in accordance with the method of claim 1.

12. The dyed membrane of claim 11, wherein the dyed membrane substantially blocks transmission of one or more wavelengths.

13. The dyed membrane of claim 11, wherein the dyed membrane has a pore having a diameter greater or equal to 0.8 km.

14. A cell culture system comprising a membrane dyed in accordance with the method of claim 1.

* * * * *